United States Patent
Michlig Gonzalez et al.

(10) Patent No.: US 10,159,653 B2
(45) Date of Patent: *Dec. 25, 2018

(54) METHODS AND COMPOSITIONS FOR INCREASING ENERGY EXPENDITURE USING CINNAMALDEHYDE

(71) Applicant: NESTEC S.A., Vevey (CH)

(72) Inventors: Stephanie Michlig Gonzalez, Le Mont-sur-Lausanne (CH); Johannes Le Coutre, Pully (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/103,458

(22) PCT Filed: Dec. 12, 2014

(86) PCT No.: PCT/EP2014/077544
§ 371 (c)(1),
(2) Date: Jun. 10, 2016

(87) PCT Pub. No.: WO2015/086811
PCT Pub. Date: Jun. 18, 2015

(65) Prior Publication Data
US 2016/0303055 A1    Oct. 20, 2016

Related U.S. Application Data

(60) Provisional application No. 61/915,298, filed on Dec. 12, 2013.

(51) Int. Cl.
| | |
|---|---|
| *A61K 9/00* | (2006.01) |
| *A23L 33/00* | (2016.01) |
| *A23L 33/10* | (2016.01) |
| *A61K 31/11* | (2006.01) |
| *A61K 36/54* | (2006.01) |
| *A61K 45/06* | (2006.01) |

(52) U.S. Cl.
CPC .............. *A61K 31/11* (2013.01); *A23L 33/10* (2016.08); *A23L 33/30* (2016.08); *A61K 9/0053* (2013.01); *A61K 36/54* (2013.01); *A61K 45/06* (2013.01); *A23V 2002/00* (2013.01)

(58) Field of Classification Search
CPC ........ A61K 31/11; A61K 36/54; A61K 33/30; A61K 33/10; A61K 45/06
See application file for complete search history.

(56) References Cited

U.S. PATENT DOCUMENTS

2013/0344215 A1* 12/2013 Young .................... A61K 36/82
426/542

FOREIGN PATENT DOCUMENTS

| | | | |
|---|---|---|---|
| CN | 1320438 A | * | 11/2001 |
| CN | 101721400 A | | 6/2010 |
| JP | 2006199647 A | | 8/2006 |
| JP | 2007535576 A | | 12/2007 |
| JP | 2010083787 | | 4/2010 |
| JP | 20010083787 | * | 4/2010 |
| KR | 20110123002 | * | 11/2011 |
| WO | WO 2008/155536 A1 | * | 12/2008 |

OTHER PUBLICATIONS

Bashan et al. (2009 why the government can't cure obesity).*
Yasuko et al. (J. Nutritional Science and Vitaminology, 2012; 58(1) Abstract only.*
Conversion Table (endmemo.com 2017).*
Friedman et al. (J. Agric. Food Chem. (2000), 48,5702-5709).*
Pezzoli et al. "Dampened neural activity and abolition of epileptic-like activity in cortical slices by active ingredients spices" Scientific Reports—4 : 6825—DOI: 10.1038/srep06825, 2014, 12 pages.
Aggarwal, Bharat B. "Targeting Inflammation-Induced Obesity and Metabolic Diseases by Curcumin and Other Nutraceuticals" Annu Rev Nutr., Aug. 21, 2010, vol. 30, pp. 173-199.
Japanese Office Action for corresponding application P2016-537463, dispatch No. 369129, dated Sep. 4, 2018, 9 pages.

* cited by examiner

*Primary Examiner* — Shirley V Gembeh
(74) *Attorney, Agent, or Firm* — K&L Gates LLP (57) ABSTRACT

Compositions comprise an amount of cinnamaldehyde that is orally tolerable, thus avoiding an unpleasant mouth feeling, and also tolerable in the gastrointestinal tract. The amount of cinnamaldehyde is effective to increase at least one of energy expenditure, sympathetic nervous system activity, or fat oxidation, relative to a composition lacking cinnamaldehyde but otherwise identical. The composition comprising cinnamaldehyde can be used in a method to support weight management or promote weight loss, a method for preventing obesity or overweight, and a method for treating obesity or overweight. In an embodiment, the composition comprising cinnamaldehyde is administered to a human. The composition comprising cinnamaldehyde may be a medicament, a food product or a supplement to a food product.

13 Claims, 6 Drawing Sheets

Fig. 1. The chemical structure of cinnamaldehyde.

Fig. 2. Proposed mechanism of increased energy expenditure from cinnamaldehyde.

Fig. 3: Change in energy expenditure after ingestion of various compounds.

Fig. 4: Change in energy expenditure (AUC) after ingestion of various compounds.

Fig. 5. Postprandial fat oxidation after ingestion of various compounds.

Fig. 6: Postprandial fat oxidation (AUC) after ingestion of various compounds.

Fig. 7. Nose temperature after ingestion of various compounds.

| Comparisons | Difference | SE | 98.33%CI | Raw p-value | Adjusted p-value |
|---|---|---|---|---|---|
| Z10 Cap vs Pl | 25.26 | 13.943 | [-9.583;60.104] | 0.0775 | 0.2325 |
| Z10 Cin vs Pl | 34.072 | 13.567 | [0.166;67.977] | 0.0162 | 0.0486 |
| Z10 CF vs Pl | 3.486 | 13.557 | [-30.394;37.367] | 0.7984 | 1 |

Fig. 8. Chin temperature after ingestion of various compounds, indicative of blood flow.

Fig. 9. Flavor intensity results from taste testing, comparing capsaicin and cinnamaldehyde.

METHODS AND COMPOSITIONS FOR INCREASING ENERGY EXPENDITURE USING CINNAMALDEHYDE

CROSS REFERENCE TO RELATED APPLICATIONS

The present application is a National Stage of International Application No. PCT/EP2014/077544, filed on Dec. 12, 2014, which claims priority to U.S. Provisional Patent Application No. 61/915,298, filed Dec. 12, 2013, the entire contents of which are being incorporated herein by reference.

BACKGROUND

The present disclosure generally relates to methods and compositions for increasing energy expenditure. More specifically, the present disclosure relates to compositions comprising cinnamaldehyde in an amount that increases energy expenditure and fat oxydation while being suitable for oral consumption.

Research on the molecular mechanisms underlying pungent sensations revealed the existence of two cation channels, TRPV1 (transient receptor potential V1) and TRPA1 (transient receptor potential A1) that are expressed in the somatosensory fibers innervating the oral cavity. TRPV1 is the receptor for heat and burning sensations such as capsaicin, the spicy compound of chili peppers. TRPA1 responds to cold and pungent compounds.

During the past decades, the prevalence of obesity has increased worldwide to epidemic proportion. Approximately 1 billion of people worldwide are overweight or obese, conditions that increase mortality, mobility and economical costs. Obesity develops when energy intake is greater than energy expenditure, the excess energy being stored mainly as fat in adipose tissue. Body weight loss and prevention of weight gain can be achieved by reducing energy intake or bioavailability, increasing energy expenditure, and/or reducing storage as fat.

The TRPV1 agonist capsaicin is well known as increasing energy expenditure and fat oxidation, but the efficient doses are intermediate to high (20 mg and more). See, e.g., Ludy et al, "The effects of hedonically acceptable red pepper doses on thermogenesis and appetite," Physiol. Behav., March 1, 102(3-4): 251-8 (2011). Moreover, capsaicin is a particularly pungent and toxic compound. Physiological effects associated with oral administration of capsaicin include a burning sensation of heat from the mid-tongue to the throat, shortness of breath, fainting, nausea, and spontaneous vomiting. As a result, only small quantities of capsaicin may be administered without causing discomfort to the individual. Food products containing capsaicin are frequently not accepted by the consumer because such products provide a very unpleasant mouth feeling. In particular, the burning effects are considered to be very unsavory, affecting the consumption of the food product.

So far, the only spice-derived ingredient showing an impact on human metabolism is capsaicin. For example, a study that looked at the effect of mustard, horseradish, black pepper and ginger on energy balance and food intake in humans did not identify any effect of these raw spices. Gregersen et al., "Acute effects of mustard, horseradish, black pepper and ginger on energy expenditure, appetite, ad libitum energy intake and energy balance in human subjects," Br. J. Nutr., 5:1-8 (July 2012). However, the effective dosage of capsaicin is too intense to be included in a food product, due to spicy taste, or to be ingested, due to gastrointestinal intolerance.

SUMMARY

Cinnamaldehyde is a $\alpha,\beta$-unsaturated aldehyde that activates TRPA1, but not TRPV1 or TRPM8, with an EC50 of approximately 60 µM. Cinnamaldehyde interacts with TRPA1 in a covalent manner. The present inventors surprisingly and unexpectedly found that cinnamaldehyde obtained a significantly higher impact on energy expenditure and sympathetic nervous system activity and an equivalent effect on fat oxidation compared to capsaicin, at a flavoring level of cinnamaldehyde judged significantly less intense than capsaicin. Consequently, unlike the spicy ingredient capsaicin, cinnamaldehyde can impact energy expenditure, sympathetic nervous system activity, and fat oxidation at concentrations in food that are tolerable both in flavor/taste and in the gastrointestinal tract.

Accordingly, in a general embodiment, the present disclosure provides a method for weight maintenance. The method comprises administering to a mammal in need thereof a composition comprising cinnamaldehyde.

In an embodiment, the cinnamaldehyde is administered in an amount of about 1.25 mg/kg body weight per day.

In an embodiment, the cinnamaldehyde is present in the composition in an amount of 17.48 ppm to 6191.0 ppm.

In an embodiment, the composition comprising cinnamaldehyde is administered once daily.

In an embodiment, the composition comprises cinnamon essential oil extract that provides at least a portion of the cinnamaldehyde.

In an embodiment, at least a portion of the cinnamaldehyde is selected from the group consisting of isolated cinnamaldehyde and synthesized cinnamaldehyde.

In another embodiment, the present disclosure provides a method for promoting weight loss. The method comprises administering to a mammal in need thereof a composition comprising cinnamaldehyde.

In another embodiment, the present disclosure provides a method for preventing obesity or overweight. The method comprises administering to a mammal at risk thereof a composition comprising cinnamaldehyde.

In another embodiment, the present disclosure provides a method for treating obesity or overweight. The method comprises administering to a mammal in need thereof a composition comprising cinnamaldehyde.

In another embodiment, the present disclosure provides a composition comprising cinnamaldehyde in an amount that is orally tolerable and effective to increase at least one of energy expenditure, sympathetic nervous system activity, or fat oxidation.

In an embodiment, the composition is a food product in which the cinnamaldehyde is present in an amount of 17.48 ppm to 6191.0 ppm.

In an embodiment, the composition is a food product comprising a component selected from the group consisting of protein, carbohydrate, fat and combinations thereof.

In an embodiment, the composition is selected from the group consisting of a medicament, a food product, and a supplement to a food product.

In an embodiment, the composition further comprises an additional ingredient in a therapeutically effective amount to promote weight maintenance or weight loss.

In another embodiment, the present disclosure provides a method for promoting weight loss. The method comprises administering a composition comprising cinnamaldehyde to an individual on a weight loss program.

An advantage of the present disclosure is to increase energy expenditure.

Another advantage of the present disclosure is to increase sympathetic nervous system activity.

Still another advantage of the present disclosure is to increase fat oxidation.

Yet another advantage of the present disclosure is to increase energy expenditure, sympathetic nervous system activity, and fat oxidation with a compound that can be easily and safely used in food products.

An additional advantage of the present disclosure is to increase energy expenditure, sympathetic nervous system activity, and fat oxidation with a naturally-occurring compound that can be found in spices.

Another advantage of the present disclosure is to increase energy expenditure, sympathetic nervous system activity, and fat oxidation with tolerable side effects or no side effects.

Yet another advantage of the present disclosure is to support weight management, promote weight loss, and/or treat or prevent obesity or overweight.

Still another advantage of the present disclosure is to increase energy expenditure, sympathetic nervous system activity, and fat oxidation with a compound that has increased acceptability, reduced pungency, and improved tolerance in the gastrointestinal tract relative to capsaicin.

Additional features and advantages are described herein, and will be apparent from, the following Detailed Description and the Figures.

DETAILED DESCRIPTION

All percentages expressed herein are by weight of the total weight of the composition unless expressed otherwise. When reference is made to the pH, values correspond to pH measured at 25° C. with standard equipment. As used in this disclosure and the appended claims, the singular forms "a," "an" and "the" include plural referents unless the context clearly dictates otherwise. As used herein, "about" is understood to refer to numbers in a range of numerals, for example the range of −10% to +10% of the referenced number. Moreover, all numerical ranges herein should be understood to include all integers, whole or fractions, within the range. The compositions disclosed herein may lack any element that is not specifically disclosed herein. Thus, a disclosure of an embodiment using the term "comprising" includes a disclosure of embodiments "consisting essentially of" and "consisting of" the components identified.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

"Overweight" is defined for a human as a BMI between 25 and 30. "Obese" is defined for a human as a BMI greater than 30. "Weight loss" is a reduction of the total body weight. Weight loss may, for example, refer to the loss of total body mass in an effort to improve fitness, health, and/or appearance. "Weight management" or "weight maintenance" relates to maintaining a total body weight. For example, weight management may relate to maintaining a BMI in the area of 18.5-25 which is considered to be normal.

As used herein, an "effective amount" is an amount that prevents a deficiency, treats a disease or medical condition in an individual or, more generally, reduces symptoms, manages progression of the diseases or provides a nutritional, physiological, or medical benefit to the individual.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human, that can benefit from the treatment.

As set forth above, the present inventors surprisingly and unexpectedly found that cinnamaldehyde obtained a significantly higher impact on energy expenditure and sympathetic nervous system activity and an equivalent effect on fat oxidation compared to capsaicin, at a flavoring level of cinnamaldehyde judged significantly less intense than capsaicin. Consequently, unlike the spicy ingredient capsaicin, cinnamaldehyde can impact energy expenditure, sympathetic nervous system activity, and fat oxidation at concentrations in food that are tolerable both in flavor/taste and in the gastrointestinal tract.

The findings of the inventors were especially surprising in that a low dose (1.25 mg/kg body weight per day) of cinnamaldehyde at a flavoring range can provide an effect after a single ingestion. In a pre-clinical study by the inventors, the dose of cinnamaldehyde was about 250 mg/kg body weight per day, with chronic ingestion (effect on body weight gain and insulin sensitivity). In the pre-clinical study, the inventors found that ingestion of a single dose of cinnamaldehyde (250 mg/kg bw) delayed gastric emptying through TRPA1 activation and reduced short term food intake. Chronic ingestion of cinnamaldehyde included in food (0.2% that represents about 250 mg/kg bw/day) reduces body weight gain of obese mice without affecting their food intake and improves their insulin sensitivity. Fat mass gain had a tendency to decrease (p 0.06), with no effect on lean mass gain.

Figure 1:
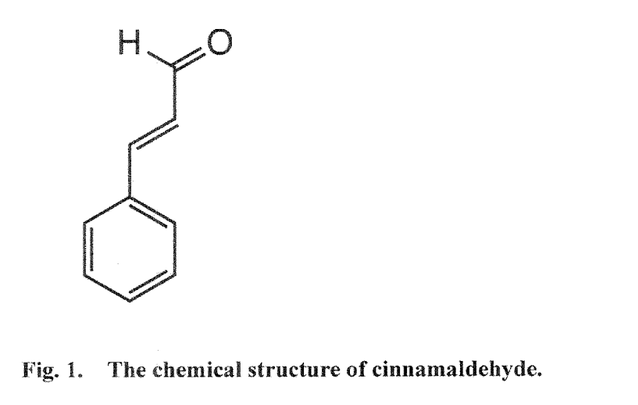
FIG. 1 shows the chemical structure of cinnamaldehyde.
Figure 2:
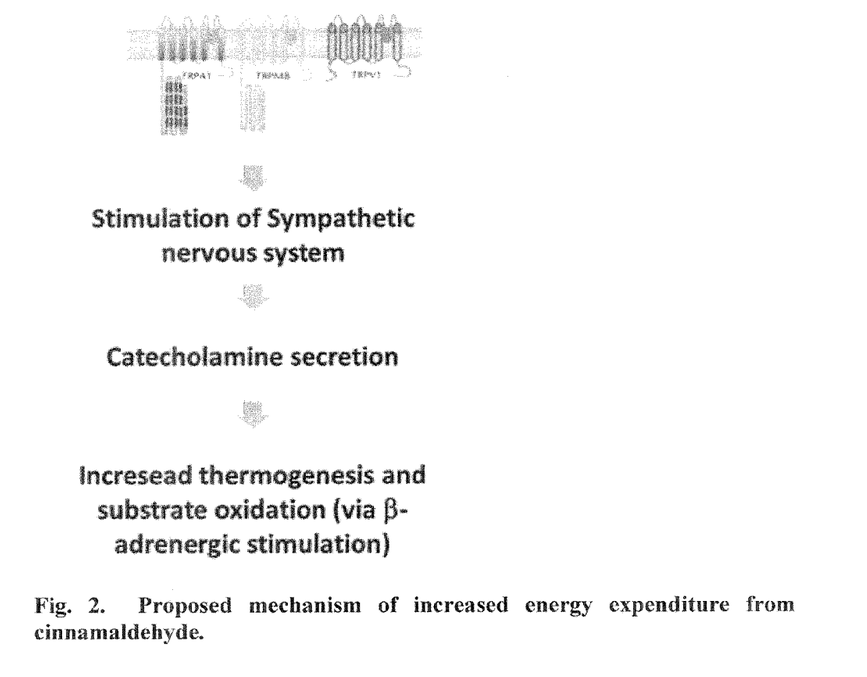
FIG. 2 shows a proposed mechanism by which cinnamaldehyde can increase energy expenditure, sympathetic nervous system activity, and fat oxidation.

Without being bound by theory, the inventors believe that cinnamaldehyde stimulates the sympathetic nervous system and, as a result, catecholamine secretion. The increased catecholamine secretion enhances thermogenesis and substrate oxidation by β-adrenergic stimulation. See FIG. 2.

Accordingly, the composition provided by the present disclosure comprises an amount of cinnamaldehyde that is orally tolerable, for example does not cause an unpleasant mouth feeling, and is effective to increase at least one of energy expenditure, sympathetic nervous system activity, or fat oxidation, relative to an otherwise identical composition lacking cinnamaldehyde. In an embodiment, the concentration of cinnamaldehyde is from 17.48 ppm to 6191.0 ppm, preferably about 350 ppm.

Cinnamaldehyde is available commercially. The cinnamaldehyde in the composition can be provided in a cinnamon essential oil extract, for example an extract from steam distillation of the oil of cinnamon bark; can be isolated cinnamaldehyde, for example isolated from cinnamon essential oil; or can be synthesized cinnamaldehyde, for example the product of aldol condensation of benzaldehyde and acetaldehyde.

In an embodiment, the composition comprising cinnamaldehyde can be used in a method to support weight management or promote weight loss. For example, the composition can be administered to a mammal managing their weight or undergoing a weight loss program, such as a weight loss diet (e.g., one or more of a low-fat diet, a low-carbohydrate diet, a low-calorie diet and a very low-calorie diet) and/or a weight loss training regimen (e.g. endurance and/or strength training). In another embodiment, the composition comprising cinnamaldehyde can be used in a method for preventing obesity or overweight by administering the composition to a mammal at risk thereof. In yet another embodiment, the composition comprising cinnamaldehyde can be used in a method for treating obesity or overweight by administering the composition to a mammal in need thereof. In an embodiment, the composition comprising cinnamaldehyde is administered to a human. The composition comprising cinnamaldehyde can be administered in an amount of about 1.25 mg/kg body weight/day in a single dose, although multiple doses are also encompassed by the present disclosure. The composition can also comprise an additional weight loss ingredient.

The composition comprising cinnamaldehyde may be a medicament, a food product, a medical food, an oral nutritional supplement, a nutritional composition, an oral cosmetics or a supplement to a food product and is preferably orally administered. A medical food product is specially formulated and intended for the dietary management of diseases or medical conditions (e.g., prevent or treat diseases or undesirable medical conditions). A medical food product can provide clinical nutrition, for example fulfilling special nutritional needs of patients with a medical condition or other persons with specific nutritional needs. A medical food product can be in the form of a complete meal, part of a meal, as a food additive, or a powder for dissolution.

A food product, medical food or nutritional composition includes any number of optional additional ingredients, including conventional food additives, for example one or more proteins, carbohydrates, fats, acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers and/or vitamins. The optional ingredients can be added in any suitable amount.

A food product, medical food or nutritional composition can be in any oral nutritional form, e.g. as a health drink, as a ready-made drink, optionally as a soft drink, including juices, milk-shake, yogurt drink, smoothie or soy-based drink, in a bar, or dispersed in foods of any sort, such as baked products, cereal bars, dairy bars, snack-foods, soups, breakfast cereals, muesli, candies, tabs, cookies, biscuits, crackers (such as a rice crackers), and dairy products.

A supplement may be in the form of tablets, capsules, pastilles or a liquid, for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

The supplement can be added in a product acceptable to the consumer as an ingestible carrier or support. Non-limiting examples of such carriers or supports are a pharmaceutical, a food composition, and a pet food composition. Non-limiting examples for food and pet food compositions are milks, yogurts, curds, cheeses, fermented milks, milk-based fermented products, fermented cereal based products, milk-based powders, human milks, preterm formulas, infant formulas, oral supplements, and tube feedings.

EXAMPLES

The following non-limiting examples present clinical scientific data developing and supporting the concept of administering cinnamaldehyde to increase at least one of energy expenditure, sympathetic nervous system activity, or fat oxidation without imparting an intolerable taste or gastrointestinal effect.

Example 1

Figure 3:
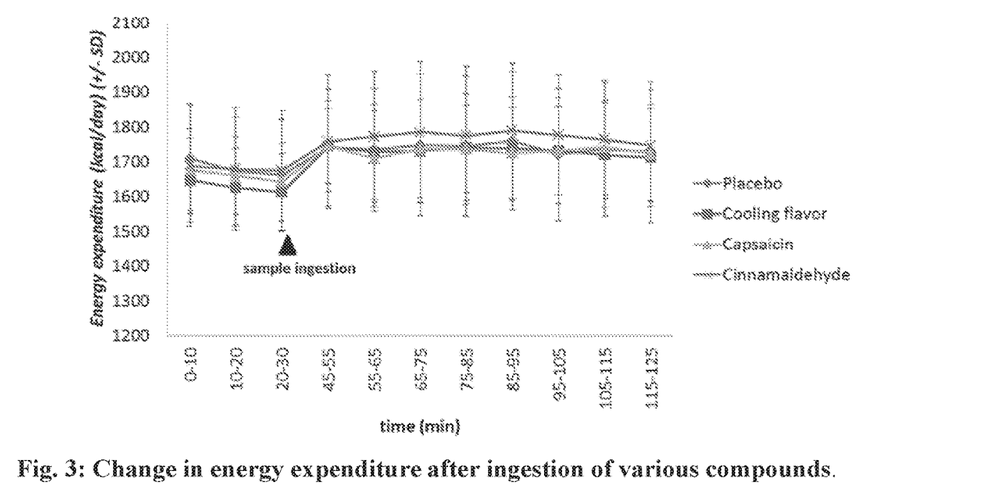
FIG. 3 shows a graph of energy expenditure as a function of time elapsed after ingestion of various compounds.
Figure 4:
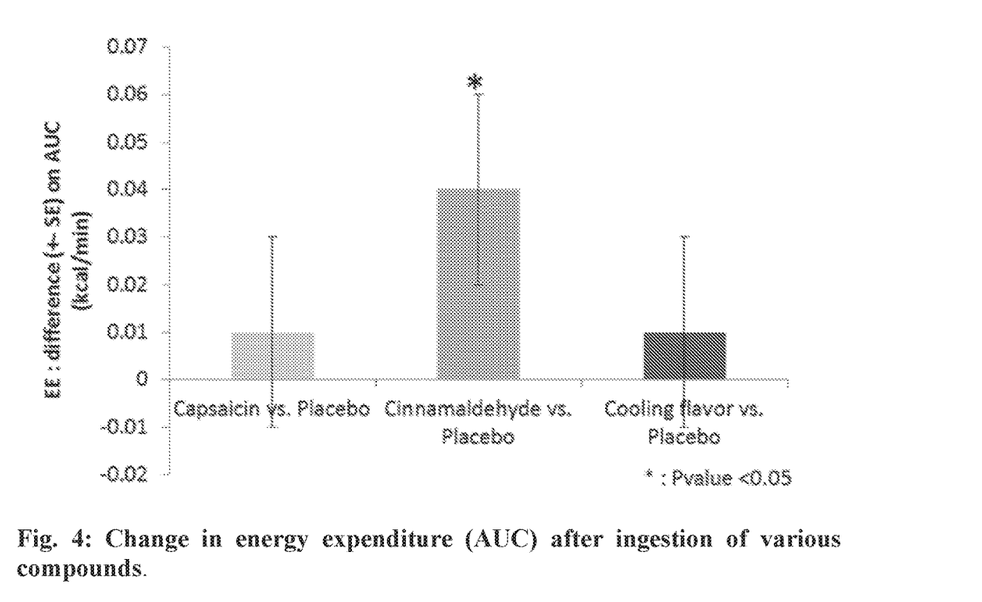
FIG. 4 shows a graph of energy expenditure based on AUC after ingestion of various compounds.

Human subjects were administered placebo, a cooling flavor, capsaicin or cinnamaldehyde. The energy expenditure was measured over the eighty minutes following ingestion. FIG. 3 shows a graph of energy expenditure as a function of time elapsed after ingestion of the various compounds. FIG. 4 shows a graph of energy expenditure based on AUC after ingestion of the various compounds. FIGS. 3 and 4 demonstrate that energy expenditure is increased after cinnamaldehyde ingestion compared to placebo.

Figure 5:
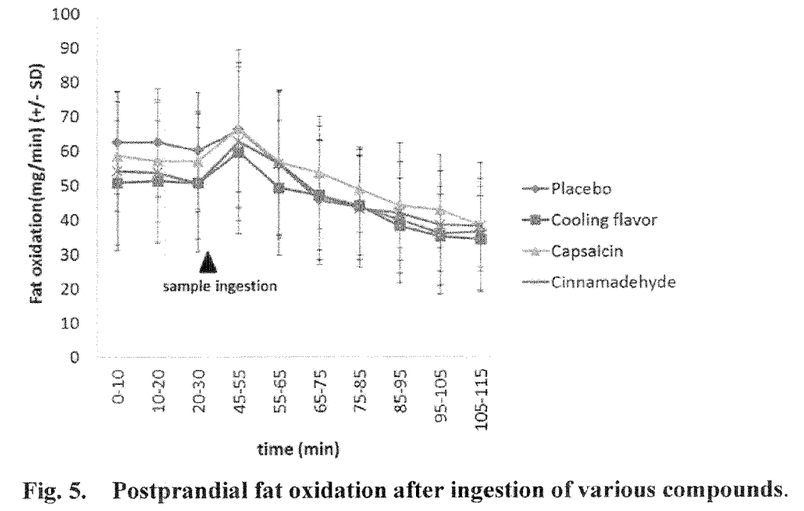
FIG. 5 shows a graph of postprandial fat oxidation as a function of time elapsed after ingestion of various compounds.
Figure 6:
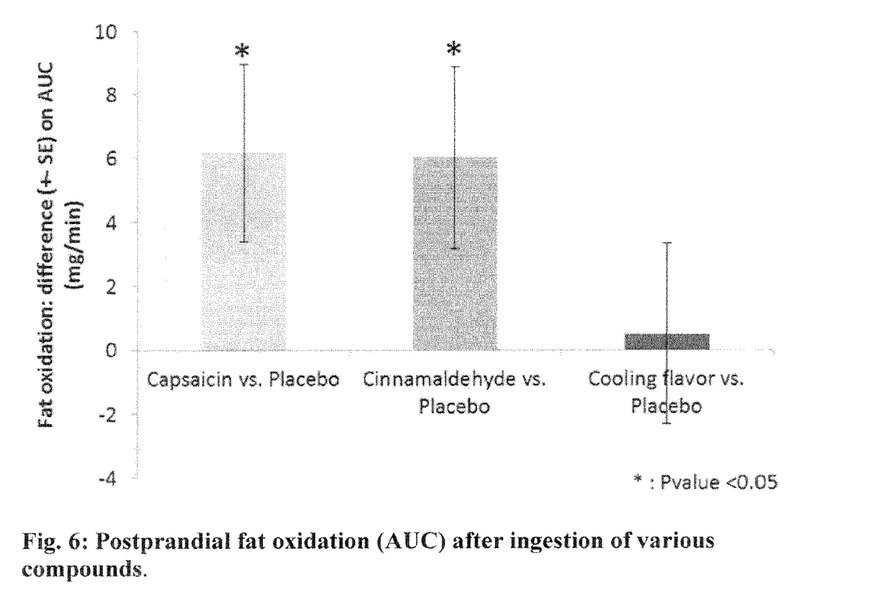
FIG. 6 shows a graph of postprandial fat oxidation based on AUC after ingestion of various compounds.

The postprandial fat oxidation was measured over the 90 minutes following ingestion of the various compounds. FIG. 5 shows a graph of postprandial fat oxidation as a function of time elapsed after ingestion of the various compounds. FIG. 6 shows a graph of postprandial fat oxidation based on AUC after ingestion of various compounds. FIGS. 5 and 6 demonstrate that postprandial fat oxidation is maintained at higher levels after cinnamaldehyde ingestion compared to placebo.

Figure 7:
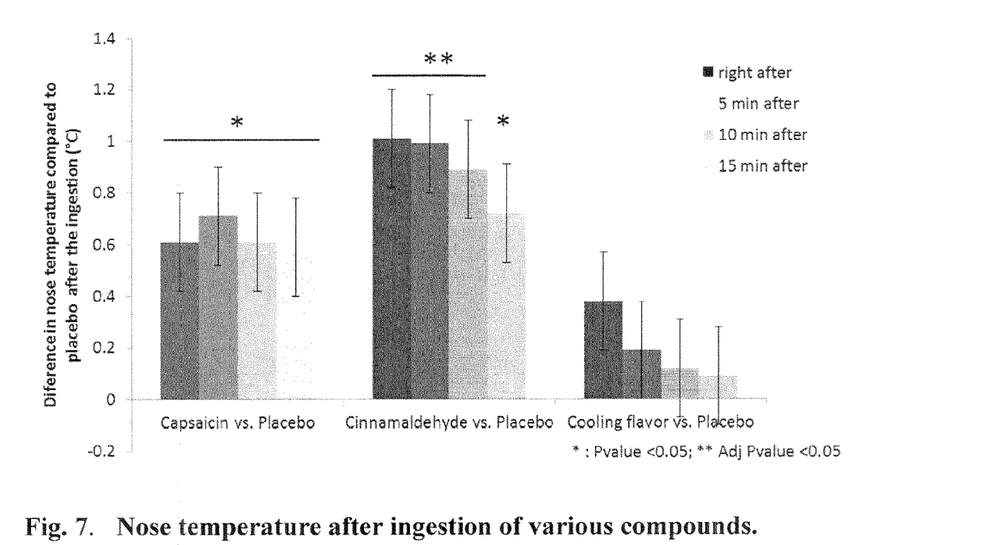
FIG. 7 shows a graph of nose temperature increases experienced after ingestion of various compounds.

The nose temperature of the subjects was analyzed over the fifteen minutes following ingestion of the various compounds. FIG. 7 shows a graph of the nose temperature increases that were experienced after ingestion of the various compounds. FIG. 7 demonstrates that capsaicin and cinnamaldehyde increase nose temperatures for the fifteen minutes following ingestion, suggesting stimulation of the same autonomic thermoregulation pathway.

Figure 8:
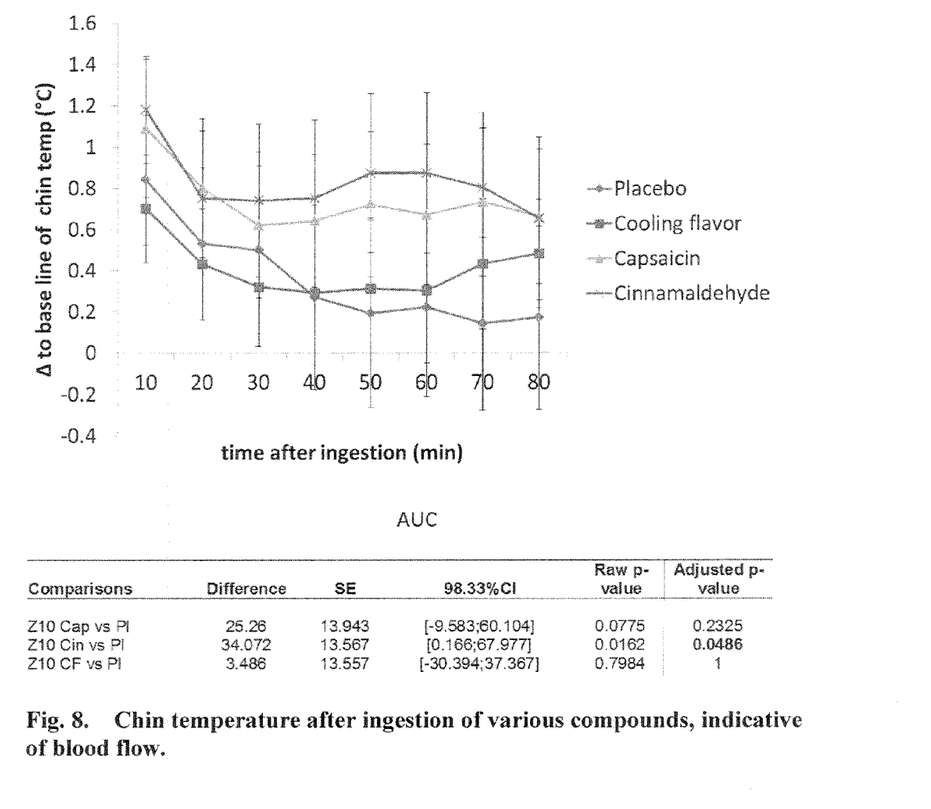
FIG. 8 shows a graph and a table of chin temperature, relative to baseline, as a function of time elapsed after ingestion of various compounds.

The chin temperature of the subjects was measured over the eighty minutes following ingestion of the various compounds. FIG. 8 shows a graph and a table of the chin temperature, relative to baseline, as a function of time elapsed after ingestion of the various compounds. FIG. 8 demonstrates that cinnamaldehyde increases chin temperature for a prolonged time after ingestion, indicating increased blood flow, probably reflecting sympathetic autonomic activity.

These results indicate that capsaicin and cinnamaldehyde might induce the same short term autonomic thermoregulation response by inducing a vasodilator reflex on the capillary of the nose. The increased sympathetic activity identified by measuring the facial temperature (increased blood flow on the chin) might explain the increased energy expenditure measured by indirect calorimetry.

Example 2

Figure 9:
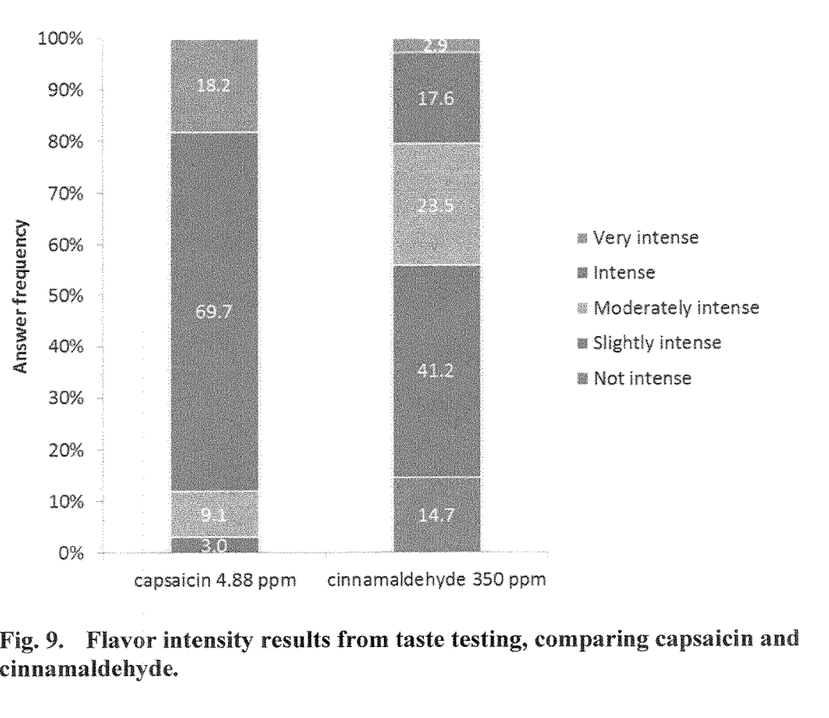
FIG. 9 shows taste testing results comparing 4.88 ppm of capsaicin and 350 ppm of cinnamaldehyde.

Human subjects were administered a composition comprising 4.8 ppm capsaicin or 350 ppm cinnamaldehyde. FIG. 9 shows a graph of the comparative taste testing results. 87.9% of the participants judged capsaicin intense to very intense, compared to only 20.5% for cinnamaldehyde. To achieve a similar effect on fat oxidation of capsaicin and cinnamaldehyde, the dose of capsaicin is about 1.5 times less than the maximum that can be used as a flavor (7 ppm according to Fenaroli's Handbook), and the dose of cinnamaldehyde is about 17.5 times less than the maximum that can be used as a flavor (6191.0 ppm according to Fenaroli's Handbook).

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of increasing at least one characteristic selected from the group consisting of energy expenditure, sympathetic nervous system activity, and fat oxidation, the method comprising orally administering to a mammal maintaining a body mass index (BMI) of 18.5-25 a composition that is a food product comprising cinnamaldehyde, and a concentration of the cinnamaldehyde in the composition is 17.48 ppm to 6191.0 ppm relative to the composition.

2. The method of claim 1 wherein the cinnamaldehyde is administered to the mammal in an amount of about 1.25 mg/kg body weight per day.

3. The method of claim 1 wherein the cinnamaldehyde is present in the composition in a concentration of about 350 ppm.

4. The method of claim 1 wherein the composition comprising cinnamaldehyde is administered to the mammal once daily.

5. The method of claim 1 wherein the composition comprises cinnamon essential oil extract that provides at least a portion of the cinnamaldehyde.

6. The method of claim 1 wherein at least a portion of the cinnamaldehyde is selected from the group consisting of isolated cinnamaldehyde and synthesized cinnamaldehyde.

7. The method of claim 1 wherein the food product comprises a component selected from the group consisting of protein, carbohydrate, fat and combinations thereof.

8. The method of claim 1 wherein the composition further comprises an additional ingredient in a therapeutically effective amount to promote weight maintenance or weight loss.

9. An orally administered composition that is a food product comprising cinnamaldehyde, wherein a concentration of the cinnamaldehyde in the composition is 17.48 ppm to 6191.0 ppm relative to the composition, the composition is effective to maintain a body mass index (BMI) of 18.5-25 and to increase at least one characteristic selected from the group consisting of energy expenditure, sympathetic nervous system activity, and fat oxidation.

10. The composition of claim 9 wherein the composition is a food product in which the cinnamaldehyde is present in a concentration of about 350 ppm.

11. The composition of claim 9 wherein the composition is a food product comprising a component selected from the group consisting of protein, carbohydrate, fat and combinations thereof.

12. The composition of claim 9 wherein the composition is selected from the group consisting of a medicament, a food product, and a supplement to a food product.

13. The composition of claim 9 wherein the composition further comprises an additional ingredient in a therapeutically effective amount to promote weight maintenance or weight loss.

* * * * *